United States Patent [19]
Gordon

[11] Patent Number: 5,408,400
[45] Date of Patent: Apr. 18, 1995

[54] DISPOSABLE STERILE COVERING FOR DENTAL AND SURGICAL LIGHTING FIXTURES

[76] Inventor: Chester D. Gordon, 1929 W. 148th St., Gardena, Calif. 90249

[21] Appl. No.: 134,583
[22] Filed: Oct. 12, 1993
[51] Int. Cl.⁶ .............................................. F21L 15/12
[52] U.S. Cl. ...................................... 362/400; 362/457; 362/804; 16/111 R; 16/114 R; 206/438; 206/524.8
[58] Field of Search ............... 362/109, 285, 376, 399, 362/400, 457, 458, 804; 206/223, 438, 524.8, 554; 16/111 R, 114 R, DIG. 19, DIG. 24; 74/558.5; 118/504, 505

[56] References Cited

U.S. PATENT DOCUMENTS

| | | | |
|---|---|---|---|
| 2,601,881 | 7/1952 | Oberlin, Sr. | 74/558.5 |
| 3,685,720 | 8/1972 | Brady | 206/438 |
| 3,951,333 | 4/1976 | Forbes, Jr. et al. | 206/438 |
| 4,777,574 | 10/1988 | Eisner | 362/399 |
| 4,795,669 | 1/1989 | Bowskill et al. | 362/804 |
| 4,810,194 | 3/1989 | Snedden | 16/111 R |
| 4,927,028 | 5/1990 | Hemm et al. | 206/524.8 |
| 4,975,826 | 12/1990 | Bell | 362/376 |
| 5,142,736 | 9/1992 | Kuehn et al. | 362/804 |

Primary Examiner—Ira S. Lazarus
Assistant Examiner—Alan B. Cariaso
Attorney, Agent, or Firm—Willie Krawitz

[57] ABSTRACT

A disposable sterile covering for the handle of a dental light or surgical light is provided for reducing the risk of contamination arising when treating patients. The sterile covering is sufficiently flexible to stretch over the entire handle of a dental light without slipping, while being sufficiently resilient to withstand gripping forces applied to its ends. One or more tear strips extend along the covering, and when the tear strips are removed, the covering will separate into two or more parts, which can then be easily removed from the light.

8 Claims, 1 Drawing Sheet

U.S. Patent    Apr. 18, 1995    5,408,400
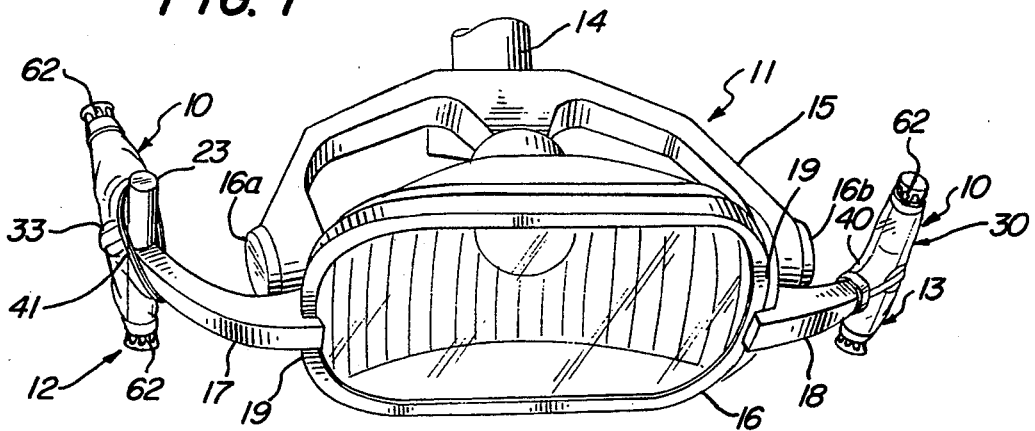
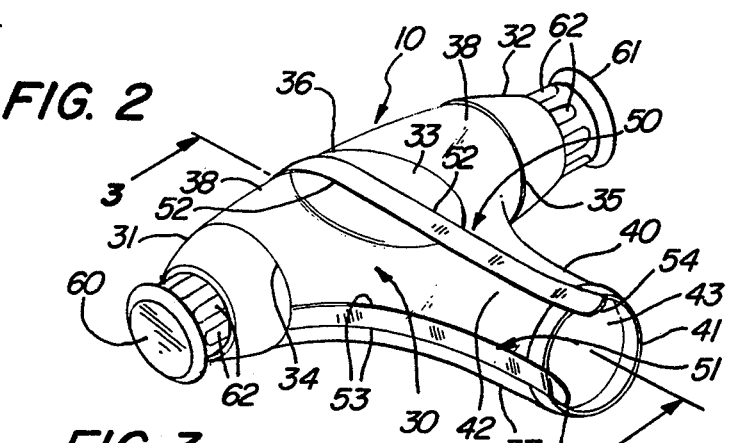
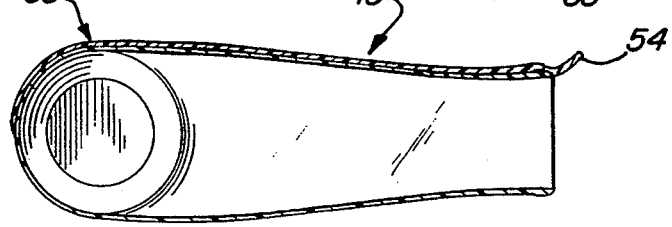
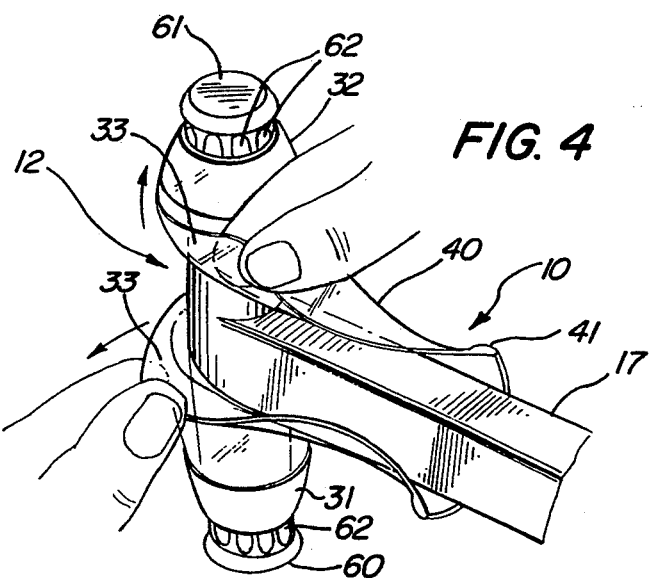

DISPOSABLE STERILE COVERING FOR DENTAL AND SURGICAL LIGHTING FIXTURES

BACKGROUND OF THE INVENTION

This invention relates to a new and improved disposable sterile covering for the handle of a positionable dental or surgical light that is subject to direct or cross-contamination during dental or medical procedures. The risk of direct or cross-contamination and the spread of disease between patients is a growing concern due to increasing evidence that AIDS, hepatitis and other diseases may retain their biologically active properties for a long period of time in a matrix of saliva, blood or other body fluids. Such a matrix can readily coat the light handle of a dental or medical light fixture during the course of a dental or medical procedure. When a dentist or physician treats additional patients, there is a risk that diseases within the matrix can be transferred to them from the handle of the light, hence risking the transfer of disease or other forms of contamination from one patient to another.

Various protective devices for reducing the risk of cross-contamination and the spread of disease between patients have been proposed, and typical prior art devices are shown in U.S. Pat. Nos.: 4,559,671; 4,605,124; 4,777,574; 4,795,669; 4,844,252; 4,975,826; 4,976,299; 5,036,446; 5,065,296; and, 5,142,736. None of these prior art devices provide a disposable covering for the handle of a dental light or other positionable lighting fixture that can he quickly and easily removed with only one hand, without touching the handle or altering the position of the light.

Also, none of these prior art devices provide a disposable, suitably shaped cover to maintain a firm grasp on the light during dental or medical procedures, especially if the cover is slippery due to saliva, blood, etc.

Consequently a need exists for a sterile, disposable covering for a wide variety of dental or surgical light handles which can be quickly installed, adjusted, and removed.

THE INVENTION

According to the invention, a disposable sterile covering is provided for reducing the risk of direct and cross-contamination arising in conjunction with the treatment of patients when time and resource constraints make impractical the repeated sterilization of the handles of dental and medical lights during dental or medical procedures.

The disposable covering comprises a thin elastic material having sufficient flexibility to stretch over the handle of the dental or surgical light, and sufficient resiliency to withstand repeated gripping forces applied to its ends.

One or more tear strips comprising a series of indentations or weakened areas extend along the disposable cover from end-to-end or side-to-side. When the tear strip is pulled, it will separate the disposable covering into two or more parts, and this in turn will allow for easy single-handed removal of the covering from the dental or medical light handle. This will eliminate the tedious and time consuming process of stretching, pulling and tearing the disposable covering during its removal.

BRIEF DESCRIPTION OF THE DRAWINGS

FIG. 1 is an external, perspective view of a positionable lighting fixture showing the sterile disposable covering of the present invention, partially and fully covering the handles of a positionable dental or surgical light;

FIG. 2 is an upper, external perspective view of the sterile disposable covering of this invention;

FIG. 3 is a sectional side elevation view of the sterile disposable covering taken along lines 3—3 of FIG. 2; and, FIG. 4 is an enlarged portion of FIG. 1 showing a disposable covering of the present invention being removed from a handle of the positionable dental or surgical light.

DESCRIPTION OF THE PREFERRED EMBODIMENTS

The sterile disposable covering 10 of this invention for reducing the risk of cross-contamination during dental and medical procedures is shown in FIG. 1, and partially and fully covers T-shaped handles 12 and 13 of a positionable light fixture 11.

The positionable lighting fixture 11 extends from and is supported by a mounting shaft 14 having a moveable, U-shaped arm support 15. The fixture includes a generally oval illuminating body 16 which is connected to the arm support 15 by swivel connectors 16a and 16b. Arm shaped posts 17 and 18 extend from each side 19 of the illuminating body 16, and the T-shaped handles 12 and 13 are mounted on the posts 17, 18; the handles define end portions 23.

During use, the T-shaped handles 12 and 13 are repeatedly adjusted by a dental or medical practitioner to illuminate a patient during the course of a dental or medical procedure. As the positionable lighting fixture is adjusted, there is a risk that the bioactive materials within a matrix of saliva, blood or other body fluids may be transferred from the handles of the positionable light fixture to other patients.

A pair of handle shaped grips 60, 61 and associated finger supports 62 enable the dental light handle to be grasped if the covering becomes too slippery due to saliva, blood or other bodily fluids.

As shown in FIG. 2, the covering 10 comprises a pillow-shaped portion 30 having rounded ends 31, 32, and a cross section which may be elliptical, oval, plano convex, etc. A central portion 33 is defined by the disposable cover, and has sufficient flexibility to stretch over the T-shaped handles 12 and 13. Also, central portion 33 is sufficiently resilient to withstand repeated grasping forces applied to its edges 34, 35, 36, and 37. A thicker and less flexible peripheral portion 38 surrounds central portion 33, and maintains a tight fit over the entire handle 12 or 13, and to transmit forces of tension to one or more tear strips, which will be described, infra.

A flexible neck 40 and end rim 41 extend perpendicularly from a point medially positioned along the lower end 42 of the covering, and the neck forms an aperture 43 which is sufficiently large to accommodate various sizes of light handles. In use, the end rim 41 is sufficiently resilient to form a tight seal around the posts 17, 18, hence maintaining the T-shaped handles sterile.

The tear strips 50 and 51 of this invention include edge-formed, weakening indentation lines 52 and 53 which extend across the pillow and neck portions, and along the surface of the disposable covering 10. The tear strips terminate near the base of the end rim 41 where they form free ends 54, 55.

As shown in FIGS. 3 and 4, when a free end is pulled, the disposable covering 10 separates along the indentation lines into two parts, and this in turn allows for easy, single-handed removal of the covering from the positionable light.

The covering 10 may be produced from a flexible plastic film such as polyethylene, polyester, nylon, polypropylene, PVC, polyvinylidene fluoride, and latex rubbers.

Typically, the dimensions of the pillow portion 30 vary from about 3–5 inches wide and about 2½–4 inches deep.

During storage, the disposable covers may be protected from handling, dust, bacteria, etc., by a vacuum seal in stackable plastic covers.

Various embodiments within the spirit of this invention are possible such as providing a covering defining a series of perforations and/or indentations, and employing a tear strip which overlies and seals the perforations and/or indentations during use. When the tear strip is stripped away from the perforations, the covering may be separated into two or more sections and removed from the handles, generally with one hand.

I claim:

1. A sterile disposable covering for a positionable medical light handle to reduce the risk of contamination during the treatment of patients, and assembly comprising:
   a.) a shaped plastic film structure adapted to be stretched around, and enclose and seal the light handle against contamination during a surgical or dental procedure; and,
   b.) at least one tear strip positioned along the surface of the disposable covering and providing an attachment edge and a free edge, the attachment edge forming at least one indentation line; whereby,
      i. during use, the disposable covering and tear strip function to seal the handle against contamination;
      ii. the disposable covering is separable into two or more pieces by pulling the free edge of the tear strip along an indentation line the separation of the covering being aided by tension forces produced by stretching action of the shaped plastic film structure; and,
      iii. removing the disposable covering from the handle.

2. The sterile, disposable covering of claim 1, in which the disposable cover can be separated into two or more parts for removal with one hand.

3. The sterile, disposable covering of claim 1, are constructed of materials selected from the class consisting of polyethylene, polyester, nylon, polypropylene, PVC, latex rubbers, and, polyvinylidene fluoride.

4. The sterile, disposable covering of claim 1, in which the indentation line comprises a series of perforations, and the tear strip is mounted over and seals the perforations and the covering.

5. A method for maintaining the sterility of a disposable plastic film covering defining a shaped structure for surgical and dental light handles, the covering being adapted to stretch over, cover and seal the light handle, the method for efficiently removing the covering comprising providing the covering with at least one tear strip and associated indentations or perforations, removing the tear strip, thereby separating the covering into at least two portions, along the indentations of perforations, the separation of the covering being aided by tension forces produced by stretching action of the shaped structure, and removing the covering portions from the light handles following use.

6. The method of claim 5, in which the two portions are removable with one hand.

7. The method of claim 5, in which the disposable covering is constructed of a material selected from the class consisting of polyethylene, polyester, nylon, polypropylene, PVC, latex rubbers and polyvinylidenefluoride.

8. The method of claim 5, in which a plurality of the disposable covers are vacuum packed and maintained in a compact, sterile stack, and free from extraneous materials.

* * * * *